United States Patent
Han et al.

(10) Patent No.: US 6,706,520 B2
(45) Date of Patent: Mar. 16, 2004

(54) ASSESSMENT OF INVASIVE POTENTIAL OF TUMOR CELLS

(76) Inventors: Kehan Han, 2255 rue Frontenac, Montreal, Quebec (CA), H2K 2Z7; Kedu Han, 4714 Mason Ct., Sugar Land, TX (US) 77479

(*) Notice: Subject to any disclaimer, the term of this patent is extended or adjusted under 35 U.S.C. 154(b) by 287 days.

(21) Appl. No.: 09/879,455

(22) Filed: Jun. 13, 2001

(65) Prior Publication Data

US 2003/0044970 A1 Mar. 6, 2003

(51) Int. Cl.[7] .................................. C12M 3/06
(52) U.S. Cl. .......................... 435/287.9; 435/297.5; 435/29; 435/34; 435/288.4; 359/398
(58) Field of Search .................. 435/29, 32, 33, 435/34, 401, 402, 287.1, 287.9, 288.2, 288.3–288.5, 297.1, 297.5, 304.2, 305.1–305.4; 359/398

(56) References Cited

U.S. PATENT DOCUMENTS

| | | | |
|---|---|---|---|
| 4,308,351 A | * 12/1981 | Leighton et al. | ......... 435/297.5 |
| 4,446,234 A | 5/1984 | Russo | |
| 4,829,000 A | 5/1989 | Kleinman | |
| 5,158,874 A | 10/1992 | Kleinman | |
| 5,840,514 A | 11/1998 | Livant | |
| 6,037,168 A | * 3/2000 | Brown | ..................... 435/288.3 |
| 6,087,157 A | 7/2000 | Badylak | |
| 6,350,610 B2 | * 2/2002 | Egger | ..................... 435/287.1 |

FOREIGN PATENT DOCUMENTS

JP 62155078 A * 7/1987 ............ C12M/1/22

OTHER PUBLICATIONS

Terranova, V.P., et al., Use of a recontituted basement membrane to measure cell invasive ness and select for highly invasive tumor cells. Proc Natl Acad Sci USA, vol. 83, pp. 465–469, 1986.
Albini, A., et al., A rapid in vitro assay for quantitating the invasive potential of tumor cells. Cancer Research, vol. 47, pp. 3239–3245, 1987.
Mackinnon, W.B., et al., Evaluation of an in vitro invasion assay for use on solid tissue samples and cultured cells. Invasion Metastasis, vol. 12, pp. 241–252, 1992.
Albini, A., Tumor and endothelial cell invasion of basement membranes. The matrigel chemoinvasion assay as a tool for dissecting molecular mechenisms. Pathology Oncology Research, vol. 4, pp. 230–241, 1998.

* cited by examiner

*Primary Examiner*—William H. Beisner

(57) ABSTRACT

The present invention provides an apparatus and methods to evaluate invasive potential of tumor cells. The apparatus permits culturing, staining and analysis of test samples to be performed on the same test plate to facilitate cell invasiveness tests. Methods for testing cell invasiveness in vitro are described.

7 Claims, 1 Drawing Sheet

ASSESSMENT OF INVASIVE POTENTIAL OF TUMOR CELLS

CROSS REFERENCE TO RELATED APPLICATIONS

Not Applicable.

BACKGROUND OF THE INVENTION

This invention relates to the assessment of invasive potential of biological cells. More specifically, this invention is directed to the testing of tumor cells for their ability to invade tissues and cause metastases.

Metastasis, i.e. the spread of tumor cells from a primary tumor to distant organs, is the major cause of death for most cancer patients. Metastatic process consists of several essential events including escape of tumor cells from the bulk tumor, survival of tumor cells in the circulation, and migration of tumor cells to distance sites where conditions are suitable for growth.

Cell invasion of basement membrane is a crucial step in the multiple steps of tumor metastasis and is pathologically considered the hallmark of a malignant tumor. Basement membranes are thin continuous layers composed of a dense meshwork of laminin, collagen, glycoprotein, proteoglycan and other components. Basement membranes normally underlie epithelia and form barriers that block the passage of cells and macromolecules. However, most malignant tumor cells have acquired ability to invade and penetrate basement membrane barriers. The process of cell invasion includes: one or more tumor cells attach to basement membrane, secret enzymes to degrade adjacent basement membrane, pass through the basement membrane barrier, and migrate into adjacent tissue.

A variety of in vitro assays have been devised for evaluating the ability of tumor cells to penetrate the basement membrane. This is done by methods known in the prior art. Isolated natural basement membrane, submucosa-derived matrix, and basement membrane matrix derived from animal or human origin have been employed for cell invasiveness assay(Russo, R et al., U.S. Pat. No. 4,446,234 (1984); Kleiman, H K et al., U.S. Pat. No. 4,829,000(1989); Kleiman, H K et al., U.S. Pat. No. 5,158,874(1992); Livant, D L. U.S. Pat. No. 5,840,514(1998); Badlak, S F et al., U.S. Pat. No. 6,087,157(2000)). For example, the basement membrane matrix can be applied directly onto a culture plate or Petri dish to form a gel-like substrate for cell growth and invasion. The tested invasive tumor cells are able to degrade the substrate and migrate toward the bottom of the plate. Invaded tumor cells could be observed at the bottom plane of the plate through a microscope. Such thick gel method requires long experimental period and is unsatisfied for quantitative purpose. At the present time conventional or modified blind well Boyden chamber assays are most widely used for quantitative analysis of cell invasiveness.

Essentially, the conventional blind well Boyden chamber assay procedure involves placing a suspension of tumor cells and a chemical agent (chemoattractant) in two separate chambers. The two chambers are separated by a membrane filter (such as polycarbonate membrane), which is coated with a thin layer of extracellular matrix (such as Matrigel®, Becton Dickinson, Bedford, Mass.). The tested tumor cells in one chamber migrate through the membrane filter into another chamber in response to chemotactic stimuli. After a predetermined period of time, the membrane filter is removed and cells on the filter surface closest to the chamber containing the cell suspension are removed. The remaining cells on the underside of the filter (i.e. the side of the filter closest to the chamber containing the chemoattractant) are then fixed and stained. Using a high power microscope, the filter is examined. The number of cells appearing on the underside of the filter is counted. This type of assay is usually referred as chemotaxis assay or chemoinvasion assay.

However, The application of blind well Boyden chamber assay involves removing the sample membranes with attached cells from the chambers after incubation. Such manipulation and following manipulations in staining process are prone to cell loss and make the cell counting inaccurate. Moreover, Invasive cells passed through the basement membrane into the lower chamber consist of two portions: one attached to the lower surface of the membrane and the other fell down at the bottom of the lower chamber. Although the cells fell down at the bottom of the lower chamber present very invasive potential, this portion of cells is usually discarded in the assay since additional procedures and time be needed to collect them. Finally, The conventional blind well Boyden chamber assay requires several preparatory steps including coating membrane, filling into lower chamber with medium with chemoattractant, assembling the upper chamber and filling into the upper chamber with cell suspension. These successive manipulations increase the interval between different samples and complicate the assay procedure.

There are several modifications of the blind well Boyden chamber applications. Some test instruments or kits are commercially available. These include: (1)transwell plate with polycarbonate membrane filter (Costar Scientific, Cambridge, Mass.), (2)multiwell plate with inserts (Becton Dickinson, Bedford, Mass.), and (3)ECM Invasion chamber including multiwell culture plate and inserts (Chemicon International, Temecula, Calif.). Although the membranes of the inserts or transwell plates are pre-coated with extracellular matrix substrate to facilitate preparatory procedure, those applications do not overcome the major disadvantages which affect the accuracy of the experiment.

There is a great need in developing a simple and more reliable device and method for evaluating cellular invasive potential of tumor cells.

BRIEF SUMMARY OF THE INVENTION

The present invention is directed to the use of a simple apparatus with a single or multi test sites for cell invasiveness analysis which requires minimum manipulation. Specifically, various procedures such as cell culturing, separating, staining, and counting invaded cells of a test sample may be performed on the same plate of the apparatus to speed up testing and to minimize the cell loss.

The major components of the apparatus comprise a supporting plate, a microporous membrane, an intermediate layer of extracellular matrix deposited between the membrane and the plate, a top layer of the extracellular matrix coated on the surface of the membrane, and a bonding element to adhere periphery of the membrane to the plate. The optimal thickness of the top layer of the extracellular matrix, the optimal thickness of the intermediate layer of the extracellular matrix between the plate and the membrane, and the optimal pore size of the membrane are selected such that the cells under study can not pass through the pores directly. In order to pass through the pores of the membrane, the tested cells must: (a) attach, digest and absorb the coated extracellular matrix to access the membrane; (b) deform and migrate through the pores of the membrane; (c) digest and absorb the extracellular matrix deposited between the membrane and the plate; and (d) migrate into the intermediate layer between the membrane and the plate. These steps mimic the process of tumor cell invasion of basement membrane in metastasis in vivo.

The present invention provides a novel in vitro assay method for quantitative analysis of cell invasiveness. With the use of the test apparatus in accordance with the present invention, the invaded cells, without the effect of chemoattractant, pass through the membrane pores and enter the intermediate layer of the extracellular matrix between the membrane and the plate. Cells that fail to invade will remain on the surface of the membrane and can be excluded during experimental process.

A variety of assay formats are contemplated for testing the invasive potential of tumor cells. In one preferred embodiment, a semisolid tumor cell suspension (as a bulk tumor) is placed on the test site of the apparatus. Thereafter, the invasiveness of tumor cells in contact with extracellular matrix-coated membrane is assessed. Alternatively, a portion of a patient's tumor is placed on the test site of the apparatus and the metastatic feature of the tumor tissue is assessed. In another preferred embodiment, a single cell suspension is placed on the test site of the apparatus, and the invasiveness of tumor cells is assessed.

Since all procedures of the cell invasiveness assay are performed on the same plate of the apparatus and all invaded cells are confined to the intermediate layer between the membrane and the plate in all manipulation steps, there are a number of advantages:

(a) there are no risks of cell loss during manipulations;
(b) all invaded cells may be counted;
(c) the invaded cells are confined near the plane that is suitable for microscopy so that the process of cell invasion can be microscopically examined at desired timepoints during the experiment period.
(d) there are no time-consuming preparatory manipulations for coating membrane and assembly of the two chambers.

It is a first object of the present invention to provide a simple apparatus and method which integrates and simplifies experimental procedure for measuring intrinsic invasiveness potential of cells, especially for malignant tumor cells.

It is a second object of the present invention to provide a method to evaluate the metastatic feature of malignant tumor specimen in vitro.

It is a third object of the present invention to provide an apparatus in which cells can be microscopically examined during experimental period.

It is a fourth object of the present invention to provide an apparatus that is inexpensive and disposable.

It is the fifth object of the present invention to provide an apparatus for the measurement of cell invasiveness using common laboratory equipment.

These and other objects and advantages of the present invention are achieved as described in the detailed description of the invention, the appended drawings and the attached claims.

DETAILED DESCRIPTION OF THE INVENTION

Figure 1:
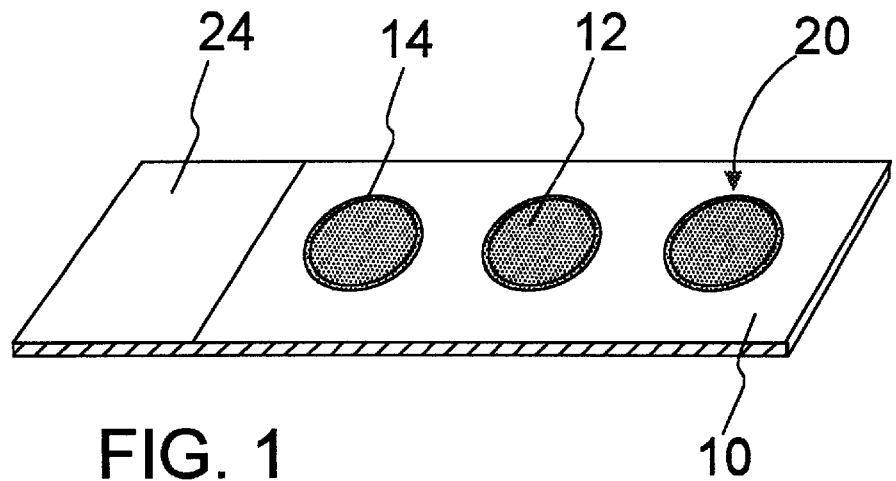
FIG. 1 is a perspective view of one preferred embodiment of the present invention, showing multiple test sites.
Figure 2:
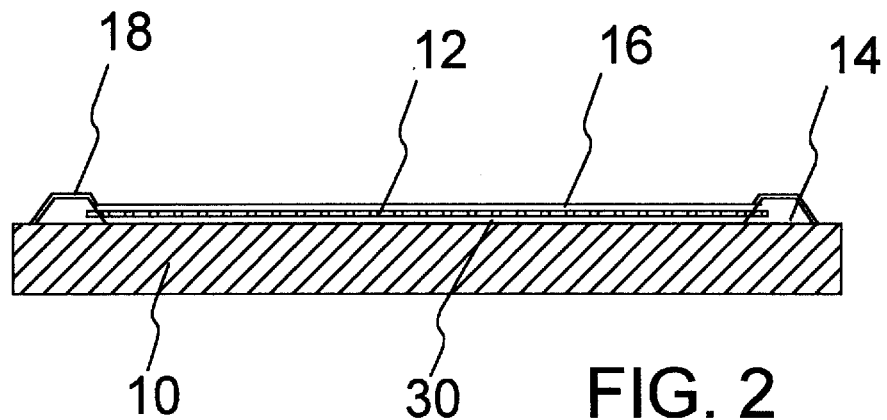
FIG. 2 is an enlarged cross-sectional view of a test site of the preferred embodiment shown in FIG. 1.

One preferred embodiment of the present invention comprises a transparent supporting plate 10 with multiple test sites 20 shown in FIG. 1. The plate 10 is preferably made of glass, such as a microscope slide. A frosted area 24 is provided for labeling samples. As shown in FIG. 2, the test site 20 comprises a membrane 12, an intermediate layer of extracellular matrix 30, a top layer of the extracellular matrix 16, and an adhesive 14 sealing the periphery and delineating the shape of test site 20. The shape of the test site may be circular, ellipse or rectangular, preferably circular. The periphery of membrane 12 is bonded to plate 10 with adhesive 14, leaving a gap of 5–50 micron between plate 10 and membrane 12 for depositing the extracellular matrix.

To obtain the intermediate layer of extracellular matrix 30, the extracellular matrix, such as Matrigel®, can be diluted with distilled water at desired concentration and filled into the gap between plate 10 and membrane 12, and air dried in a laminar flow hood. The thickness of rehydrated intermediate layer of the extracellular matrix 30 varies with the type of cell being studied, usually 5–50 micron, but will not excess a rounded diameter of a tested cell. The adhesive is made of hydrophobic material, such as resin. As shown in FIG. 2, the adhesive is also employed as a ridge around the periphery of the test site to prevent spread of culture medium from the test area. The height of the ridge of adhesive 14 is 50–500 micron. A thin layer of a water-repelling material 18, such as wax, is applied onto top and outside surface of the ridge of adhesive 14 for additionally preventing spread of culture medium from the test area. The water-repelling material can be painted, sprayed, or printed onto the top and outside surface of the ridge of adhesive 14. The top layer of the extracellular matrix 16 is coated on the upper surface of membrane 12. The thickness of the coating varies with the type of cells being studied, usually 5–50 micron. The extracellular matrix, such as Matrigel®, can be diluted with distilled water at desired concentration and spread evenly onto the surface of the membrane, and air dried in a laminar flow hood.

One technique for obtaining a specific gap size is to deposit a uniform thickness of material on the plate or the membrane equal to the thickness of the desired gap before bonding them together. A second technique is to use an adhesive that can be applied in thin lines along the periphery of the membrane such that the capillary action of the fluid adhesive between the plate and the membrane produces the desired gap. A third technique is to add a thin washer at desired thickness between the periphery of the membrane and the plate. A fourth technique is to machine impress or mold the depressions in test site before bonding the periphery of the membrane to the plate. The gap between the plate and the membrane must be carefully maintained during bonding. After bonding, the gap size is measured with the aid of a microscope. The plates may be sorted into different groups according the size of the gaps.

The supporting plate is constructed from optical quality transparent materials, preferably made of glass or plastic, such that the cells migrated through the pores of the membrane can be viewed using a microscope, either while the cells are migrating, or after the cells have been fixed and stained.

The membrane is constructed from materials that have smooth glass-like surface for clearer observation. Those materials are non-reactive to most stains for less background interference, and are non-toxic to biological cells for growing and migrating. The pore diameter of the membrane is 5–12 micron, usually 8 micron, according to cell size to be studied. Such materials include polycarbonate, cellulose, and polyester.

The extracellular matrix substrate is derived from mammalian or human origin, such as Matrigel®, submucosa-derived matrix. Such substrates are soluble or in a fluidized form at 4° C., but will polymerize into a gel-like form at 37° C.

The adhesive is constructed from materials which are hydrophobic and non-toxic to biological cells, such as resin. The adhesive can be applied in various viscosities or multiply applied to bond the membrane and the plate as well as to form the desired height of the ridge.

The material 18 is constructed from materials those are water repelling and non-toxic to biological cells, such as wax.

Figure 3:
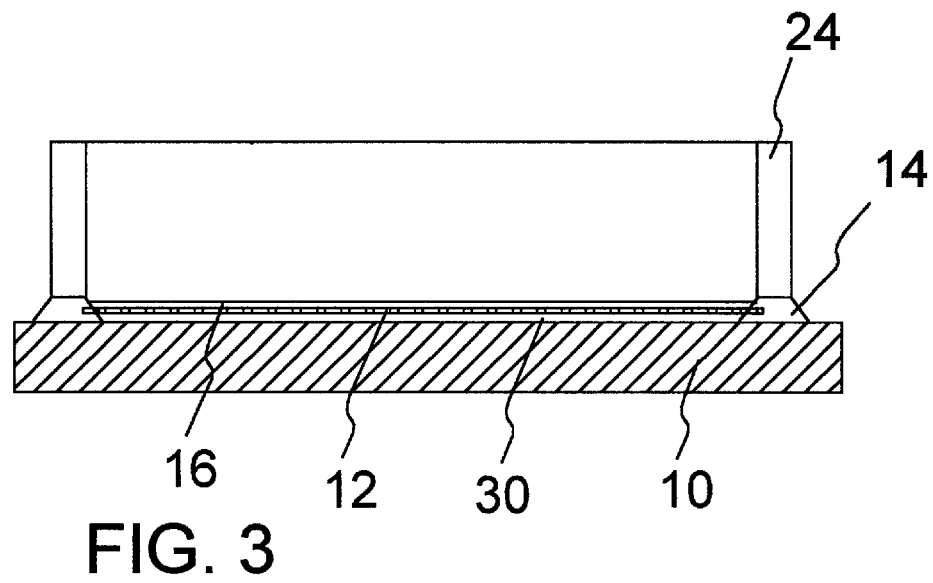
FIG. 3 is an enlarged cross-sectional view of another preferred embodiment in accordance with the present invention, showing a test site with a wall member.

In another preferred embodiment in accordance with the present invention, as shown in FIG. 3, each test site has a cylindrical wall member 24, which releasably adheres to the periphery of the test site to form a reservoir which holds the mixture of cells or tissue and culture medium. A bonding element seals and releasably bonds the lower edge of cylindrical wall member 24 to the upper surface of the ridge of adhesive 14 in a watertight manner. The periphery of membrane 12 is bonded to glass plate 10 with adhesive 14, leaving a gap of 5–50 micron between plate 10 and membrane 12 for depositing the extracellular matrix. The ridge of adhesive 14 exhibits stronger adhesion to the plate than to the lower edge of cylindrical wall member 24. Therefore, the adhesive 14 and the membrane remain adhered to the plate after separation of the cylindrical wall member from the test site. The thickness of rehydrated intermediate layer of the extracellular matrix 30 varies with the type of cell being studied, usually 5–50 micron, but will not excess a rounded diameter of a tested cell. The ridge of adhesive 14 delineates the shape of the test site. The upper surface of membrane 12 is coated with the top layer of the extracellular matrix 16. The thickness of the coating varies with the type of cells being studied, usually 5–50 micron.

The cylindrical wall member can be constructed from glass, plastic, acrylic, silicone or other materials those are hydrophobic and non-toxic to biological cells, preferably made of transparent acrylic or plastic. The height of the cylindrical wall member is 5–10 millimeter.

The bonding element, which seals and bonds the lower edge of wall member 24 to the upper surface of the ridge of adhesive 14, is constructed from materials those are hydrophobic and non-toxic to biological cells, such as resin or silicone. Preferably the bond strength of the bonding element to the wall member is stronger than to the surface of the ridge of adhesive 14. Such that the bonding element will be removed together with the wall member when the wall member is separated from the test site.

Because cell culture techniques must be performed under aseptic conditions, all components of the present invention should be sterilized. Sterilization techniques which do not significantly affect biological properties of the extracellular matrix substrate are known to those skilled in the art.

Due to the barriers of extracellular matrix, the normal cells usually do not pass through the pores of the membrane. However, under certain conditions, the cells acquire such ability to digest and absorb the extracellular matrix, such that they can pass through the membrane and migrate into the intermediate layer of the extracellular matrix between the membrane and the plate. Such mobile cells include macrophages, monocytes, neutrophils, fibroblasts and endothelial cells. Many tumor cells have acquired ability to digest and absorb the extracellular matrix. The capability of digesting and absorbing extracellular matrix of malignant tumor cells is an important feature for metastasis.

An experiment for cell invasiveness assay is performed in sterilized environment. In accordance with the first preferred embodiment, the plate with one or more test sites is placed in a culture vessel, such as a Petri dish. Firstly the extracellular matrix-coated membrane of the test site is rehydrated with distilled water. Then the certain amount of cells in medium is applied on the test site. The cells on the test site are incubated at 37° C., 5% $CO_2$ for 6–24 hours. The incubation time dependents on the density of seeded cells on the test site, thickness of the extracellular matrix coating, and the cells studied. During the incubation period, the invaded and non-invaded cells can be conveniently examined through an inverted microscope.

To quantify the result, the cells on the plate may be fixed and stained after incubation. To do this, a fixative such as 10% formaldehyde, ethanol or methanol is pipetted onto the site to fix the cells. The fixative is then pipetted out and a staining solution such as hematoxylin-eosin solution or 0.1% crystal violet solution is pipetted onto the site. The staining solution is then removed and a buffer solution such as phosphate-buffered saline(PBS) is pipetted onto the test site to rinse out residue of the staining solution. Then all the cells remaining on the surface of the membrane are thoroughly wiped out with swabs, and leave the cells in the intermediate layer of the extracellular matrix between the membrane and the plate intact. Then the invaded cells are counted and analyzed under a common microscope.

Another application in accordance with the preferred embodiment is to evaluating invasiveness of surgical resected tumor samples. The plate with one or more test sites is placed in a culture vessel, such as a Petri dish. Firstly the extracellular matrix coated membrane of the test site is rehydrated with distilled water. Then the certain amount of tumor tissue fragments is applied on the test site. The tumor tissue fragments on the test site are incubated at 37° C., 5% $CO_2$ for one to several days. The incubation time dependents mainly on the type of tissue studied. During the incubation period, the occurrence of cell invasion of tumor tissue fragments can be microscopically monitored. After incubation, the tissue fragments on the surface of the membrane are removed. After fixation, staining, and rinsing, the cells on the surface of the membrane are thoroughly wiped out with swabs, and leave the cells in the intermediate layer of the extracellular matrix between the membrane and the plate intact. The invaded cells can then be characterized and analyzed under a common microscope.

In accordance with another preferred embodiment, as shown in FIG. 3, a wall member is bonded on the test site to form a well holding culture medium. Firstly the extracellular matrix-coated membrane of the test site is rehydrated with distilled water. Then the certain amount of cells in culture medium is applied into the well. The cells are incubated at 37° C., 5% $CO_2$ for 6–12hours. The incubation time depends on the density of seeded cells on the test site, the thickness of the extracellular matrix coating, and the cells studied. During the incubation period, the invaded and non-invaded cells can be examined through an inverted microscope. After incubation, the culture medium is removed. After the cells are fixed, stained, rinsed, the wall member is removed. All the cells on the surface of the membrane are thoroughly wiped out with swabs, and leave the cells in the intermediate layer of the extracellular matrix between the plate and the membrane intact. The invaded cells can ten be counted and analyzed under a common microscope.

EXAMPLES

The following examples serve to illustrate certain preferred embodiments and aspects of the present invention and are not to be construed as limiting the scope thereof.

Example 1

Assessing Invasive Potential of Tumor Cells

In this example, the invasive behaviors of human metastatic prostate cancer cells and human urinary bladder cancer cells were evaluated. Human prostate cancer cell line PC-3 was originally cultured from a bone metastasis. Human urinary cancer cell line T24 (HTB-4) was originally cultured from a bladder transitional cell carcinoma. These cell lines were cultured until 80–90% confluence. Cells were harvested by rinsing in PBS, followed by brief treatment with 0.25% trypsin, 0.02% EDTA, and pelleting and resuspension in the appropriate medium with or without 5% fetal bovine serum (FBS) at a density of about $5 \times 10^6$ cells per ml. A solution of 5% agar in water was diluted with appropriate medium to 1% concentration and kept at 42° C., then cell suspension was mixed with 1% agar solution at a ratio of 1:1. A volume of 0.2 ml cell suspension ($5 \times 10^5$ cells) was added onto each single test site and placed them at room temperature until semi-solidified. While not limited in any mechanism, the cells were in such an environment that anchorage-independent cells (such as transformed malignant cells) could be grown preferentially while anchorage-dependent cells (such as normal cells) grow poorly. The test site serves as an artificial basement membrane and the semisolid cell suspension mimics a bulk tumor. Cells those contact the membrane may present their invasive abilities and the rest cells those do not contact with the membrane provide an environment which is unfavorable to normal cell growth but is favorable to tumor cell growth. The cells were incubated at 37° C., 5% $CO_2$ for 12 hours. After incubation, the semi-solid cell suspension was generously removed with swab from the membrane surface. A solution of 4% formaldehyde in PBS was used for fixing the cells for 10 minutes. After rinsing with PBS, the cells were stained with 0.1% crystal violet for 15 minutes and rinsed with PBS. The membrane surface was thoroughly wiped with swabs to eliminate all non-invaded cells. The invaded cells were then counted under light microscope. The result shown that the number of invaded PC-3 cells increased 3.3 times with the presence of 5% FBS and the number of invaded T24 cells increased 3.9 times with the presence of 5% FBS in which various growth factors exist. Alternatively, chemokinetic factors, growth factors or certain drugs might be applied to treat cells to observe their effects on cell invasiveness.

If the amount of tested cells available is limited for experiment then few drops of cell suspension in liquid medium can be applied directly onto the test sites with wall members, as shown in FIG. 3 in another preferred embodiment. In this case, the required amount of cells is usually ten times less than that is in semi-solid medium because all tested cells fall down onto the surface of the membrane of the test site. And the incubation time is usually less than 6 hours.

Example 2

Evaluating Invasive Potential of Resected Tumor Tissues

In this example, the invasive potential of human bladder cancer tissue was evaluated. Human bladder cancer specimen was obtained from surgically removed human bladder transitional cell carcinoma. The tumor specimen was rinsed with antibiotics (such as penicillin, streptomycin) and PBS, and cut into small fragments at about 1 $mm^3$ size. A few fragments were placed separately on a single test site, which was pre-rehydrated with distilled water. Then few drops of culture medium were added onto the test site. In some cases, a warm (42° C.) medium containing 0.5% agar might be applied to cover all fragments and the surface of the test sites. The test apparatus was incubated at 37° C., 5% $CO_2$ from one to several days until, through the inverted microscopic examination, invasion occurred in some test sites for appropriate evaluation. The specimen and semi-solid agar were removed. The cells invaded into the intermediate layer of the extracellular matrix were fixed, stained and analyzed under a common microscope.

We claim:

1. A cell invasiveness test apparatus comprising: a transparent plate having a top surface, said top surface having at least one test site, said test site comprising:
   (a) a microporous membrane filter having an upper surface and an undersurface,
   (b) an intermediate layer of extracellular matrix deposited between the undersurface of said membrane filter and the top surface of said plate,
   (c) a top layer of the extracellular matrix coated on the upper surface of said microporous membrane filter,
   (d) bond means bonding and sealing the periphery of said membrane filter on the top surface of said plate.

2. The cell invasiveness test apparatus of claim 1, wherein said transparent plate is constructed of glass or plastic, preferably a slide for microscopy.

3. The cell invasiveness test apparatus of claim 1, wherein said microporous membrane filter is a hydrophilic membrane filter, preferably constructed of polycarbonate.

4. The cell invasiveness test apparatus of claim 1, wherein said microporous membrane filter comprises pores with diameter of 2–12 micron, preferably of 8 micron.

5. The cell invasiveness test apparatus of claim 1, wherein said bond means is a hydrophobic adhesive, preferably constructed of resin.

6. A method for performing cell invasiveness tests, comprising:
   (a) providing a cell invasiveness test apparatus of claim 1;
   (b) placing tumor cells in suspension on said test site of said apparatus;
   (c) incubating said cell invasiveness test apparatus for a period of time sufficient to allow the cells digesting, absorbing contacted extracellular matrix, and passing though pores of said membrane filter;
   (d) removing cells and the top layer of the extracellular matrix from the upper surface of said membrane filter; and
   (e) determining the number of invasive cells those absorbing the extracellular matrix, passing through said membrane filter and invading into the intermediate layer of the extracellular matrix between said membrane filter and said plate.

7. A method for performing cell invasiveness tests, comprising:

(a) providing a cell invasiveness test apparatus of claim 1;
(b) placing tumor fragments on said test site of said apparatus;
(c) placing liquid or semisolid medium onto tumor fragments and said test site of said apparatus;
(d) incubating said cell invasiveness test apparatus for a period of time sufficient to allow the cells escaping from said tumor fragments, digesting, absorbing contacted extracellular matrix, and passing though pores of said membrane filter;
(e) removing tumor fragments, semisolid medium, and the top layer of the extracelluar matrix from the upper surface of said membrane filter; and
(f) determining the number of invasive cells those absorbing the extracellular matrix, passing through the membrane filter and invading into the intermediate layer of the extracellular matrix between said membrane filter and said plate.

* * * * *